United States Patent [19]

Carroll et al.

[11] Patent Number: 4,571,748
[45] Date of Patent: Feb. 25, 1986

[54] FRAMELESS GOGGLE AND METHOD OF MAKING THE SAME

[75] Inventors: John E. Carroll; Joseph R. McNeal, both of Ketchum, Id.

[73] Assignee: Scott USA Limited Partnership, Sun Valley, Id.

[21] Appl. No.: 460,510

[22] Filed: Jan. 24, 1983

[51] Int. Cl.[4] .............................................. A61F 9/02
[52] U.S. Cl. .......................................... 2/436; 2/439
[58] Field of Search ................... 2/436, 437, 439, 431, 2/432, 433, 434, 447, 435

[56] References Cited

U.S. PATENT DOCUMENTS

| | | | |
|---|---|---|---|
| 540,746 | 6/1895 | Lamb | 2/439 |
| 1,123,376 | 1/1915 | Rextrew . | |
| 1,562,350 | 11/1922 | Luckey . | |
| 2,537,275 | 1/1951 | Malcom, Jr. | 2/436 |
| 2,619,644 | 12/1949 | Christensen et al. . | |
| 2,642,568 | 6/1953 | Stewart . | |
| 2,665,686 | 1/1954 | Wood et al. | 2/435 X |
| 2,680,882 | 6/1954 | Hirschmann et al. . | |
| 3,012,248 | 12/1961 | Kleinman . | |
| 3,377,626 | 4/1968 | Smith | 2/435 |
| 3,395,406 | 8/1968 | Smith . | |
| 3,671,976 | 6/1972 | Johnson et al. | 2/430 |
| 3,691,565 | 9/1972 | Galonek . | |
| 3,718,937 | 3/1973 | Smith . | |
| 3,791,722 | 2/1974 | Ahlberg et al. . | |
| 3,858,242 | 1/1975 | Gooding . | |
| 3,945,044 | 3/1976 | McGee et al. . | |
| 4,149,276 | 4/1979 | Castro | 2/437 |
| 4,150,443 | 4/1979 | McNeilly | 2/436 |
| 4,290,673 | 9/1981 | Yamamoto | 2/437 X |

FOREIGN PATENT DOCUMENTS 0930735  7/1963  United Kingdom ................... 2/436

OTHER PUBLICATIONS

Brochure for Hydron "Thermaflex Fogeater", National Hydron Inc., East Petersburg, PA 17520.

Primary Examiner—Peter Nerbun
Attorney, Agent, or Firm—Jenner & Block

[57] ABSTRACT

A frameless goggle construction including an elongated lens structure having opposed ends formed of a generally planar, semi-rigid, transparent sheet of plastic deformed about its minor dimension to be configured as a simple curve with convex and concave sides. The sheet rigidity is such that the lens structure may flex to move the ends closer to or further from each other and the periphery of the concave side mounts a layer of soft resilient cushioning material of substantial thickness adapted for cushioned contact with and conformance to the face of a wearer of a goggle. An elongated strap is connected to the ends of the lens structure to secure the goggle to the head of the wearer and to provide a face conforming force to the lens. The lens structure is antifogging and formed of a non-rigid spacer sandwiched between inner and outer lenses with air flow passages formed in the spacer and inner lens.

14 Claims, 4 Drawing Figures

FRAMELESS GOGGLE AND METHOD OF MAKING THE SAME

FIELD OF THE INVENTION

This invention relates to goggles and methods of manufacturing them. More specifically, it relates to goggles of the sort that are mass merchandised for use by a large variety of people having widely varying facial shapes and characteristics, all of which are preferably accommodated by a single goggle size.

BACKGROUND OF THE INVENTION

Prior art of possible relevance includes U.S. Pat. Nos. 1,123,376 to Rextrew; 1,562,350 to Luckey; 2,619,644 to Christensen et al; 2,642,568 to Stewart; 2,680,882 To Hirschmann et al; 3,012,248 to Kleinman; 3,395,406 to Smith; 3,691,565 to Galonek; 3,718,937 to Smith; 3,791,722 to Ahlberg et al; 3,858,242 to Gooding; and 3,945,044 to McGee et al. In addition, so-called thermal lenses employing two plastic lenses held in spaced relation and with their interface sealed by a flexible spacer and commercially available for use in ski goggles are prior art.

Many recreational activities or sports in which large numbers of people participate require the use of goggles. Skiing and motorcycle racing are but two examples. The large number of participants require manufacture of goggles on a large scale so that they may be mass merchandised.

Even limiting consideration to the adult portion of participants in such activities, one will readily appreciate that the persons utilizing such goggles have wisely varying facial and head characteristics due to differences in sex, physical stature, head shape, and even national origin. Thus, it has been desirable, in order to minimize tooling requirements in the manufacture of such goggles, to provide goggle constructions which readily and satisfactorily adapt to the individual characteristics of a particular purchaser. In other words, to achieve economies of scale in manufacturing, it is desirable to minimize the differing number of goggle constructions and yet provide a product that can be satisfactorily worn by a large majority of the prospective purchasers.

Heretofore, this goal has been achieved through the use of a goggle frame which houses the lenses employed in the goggle. In the usual case, the frame is made of a rubberized plastic with sufficient rigidity to grip a lens and yet with sufficient pliability so as to deform somewhat under forces applied thereto by a goggle strap about the head of the wearer so as to more closely conform to the facial shape of the wearer. Examples of such goggles are shown, for example, in the previously identified U.S. Pat. Nos. 3,395,406; 3,718,937; and 3,945,044.

While these goggles have worked extremely well for their intended purposes, those skilled in the art will immediately recognize that the goggle frames must be molded and are of intricate configuration requiring quite expensive tooling. Thus, such goggles are necessarily sold at relatively high cost in order to enable the manufacturer to recapture his tooling costs.

Attempts have also been made to devise goggles that do not require a frame. One example is illustrated in the previously identified U.S. Pat. No. 1,123,376. While such goggles may work well for many purposes, they are not susceptible to use by a large variety of persons having differing facial characteristics. Specifically, the goggles thus formed are extremely rigid, in a large part due to the fact that the goggle lens employs a compound curve, and thus, the goggle cannot flex under forces applied to it by the strap to readily and fully conform to the face of the wearer.

Furthermore, the formation of the lenses of such goggles as compound curves complicates the manufacturing effort and/or increases the cost of tooling thereby adding to the ultimate cost of the goggle.

The present invention is directed to overcoming one or more of the above problems.

SUMMARY OF THE INVENTION

The principal object of the invention is to provide a new and improved frameless goggle and a method of making the same. More specifically, it is an object of the invention to provide a frameless goggle which can be worn by any of a large variety of people having vastly varying facial characteristics and yet conform to the faces of the wearer in a satisfactory fashion.

An exemplary embodiment of a frameless goggle made according to the invention includes an elongated lens structure having opposed ends and formed of a generally planar semi-rigid transparent sheet of substantially uniform thickness plastic. The lens is deformed about its minor dimension to be configured as a simple curve such that the lens structure has concave and convex sides. The sheet is such that the lens structure may flex to move the ends closer to or further from each other.

The periphery of the concave side of the lens mounts a layer of soft resilient cushioning material of substantial thickness for cushioned contact with and conformance to the face of a wearer of the goggle and an elongated strap is connected to the ends of the lens structure.

In a preferred embodiment, the lens structure includes inner and outer transparent lenses in approximately parallel spaced relation along with means interconnecting the lenses to maintain the spaced relation.

In a highly preferred embodiment, the interconnecting means seal the interface of the lenses inwardly of the edges thereof to define a thermal lens structure and means are provided in the interconnecting means and the inner lens which define anti-fogging vents for allowing the flow of air to the concave side of the inner lens.

In a highly preferred embodiment, the interconnecting means is formed of a closed cell foam disposed between the lenses and the anti-fogging defining means includes channels in the foam extending to respective openings in the inner lens.

The invention also contemplates a method of manufacturing a frameless goggle construction which includes the steps of stamping an elongated semi-rigid lens having opposed ends out of a generally planar sheet of transparent plastic material, providing a slot in each of the ends of the lens, curving the lens in the form of a simple curve such that it has a convex and a concave side, adhering a strip of foam to the concave side of the lens about the periphery thereof, and disposing an elastic strap in the slots.

Other objects and advantages will become apparent from the following specification taken in connection with the accompanying drawings.

DESCRIPTION OF THE PREFERRED EMBODIMENT

Figure 1:
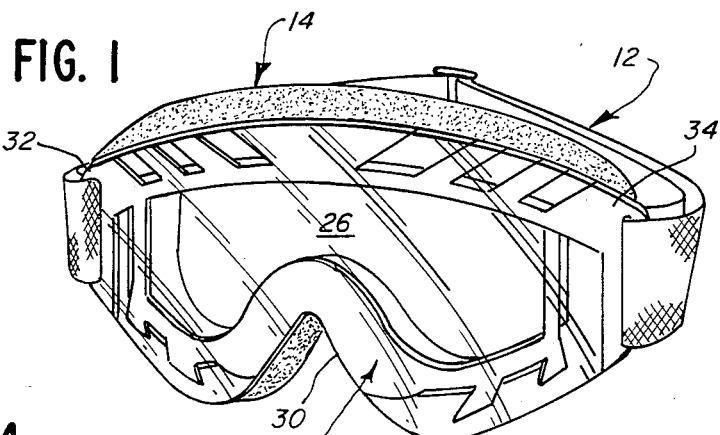
FIG. 1 is a perspective view of a frameless goggle made according to the invention.

An exemplary embodiment of a frameless goggle construction made according to the invention is illustrated in the drawings and with reference to FIG. 1 is seen to consist essentially of three components, namely, a lens structure generally designated 10, an adjustable, elastic strap, generally designated 12, of conventional construction, and a cushion, generally designated 14.

In a highly preferred embodiment, the lens structure 10 is a so-called thermal lens although it is to be understood that the invention is not limited thereto. In any event, the lens structure 10 is formed of an outer lens 16 and an inner lens 18, both stamped from a generally planar sheet of transparent, semirigid plastic, the sheet being of uniform thickness.

The lenses 16 and 18 are assembled and spaced in parallel relation by an interconnecting means 20. The interconnecting means is preferably a closed cell, flexible foam which is bonded to the lenses 16 and 18 in any suitable fashion so as to to seal against both. The interconnecting means 20 is located in close proximity to the peripheral edges 22 and 24 of the lenses 16 and 18 respectively, and extends peripherally thereabout to define a central viewing area 26. Because the interconnecting means 20 seals against both the lenses 16 and 18, the space 28 between such lenses and the central viewing area 26 is sealed to provide a thermal lens as mentioned.

As best seen in FIG. 1, the lenses 16 and 18 are horizontally elongated and intermedate their ends each is provided with a downwardly opening recess 30 to accomodate the nose of a wearer.

The lens structure 10 is deformed from the plane of the plastic sheets making up the lenses 16 and 18 into a simple curve, as opposed to a compound curve. That is, for all horizontal sections taken through the lens structure 10 at any point thereon, the curve will have essentially the same profile. Stated another way, the lens is curved only about its minor dimension and not about both minor and major dimensions.

Figure 2:
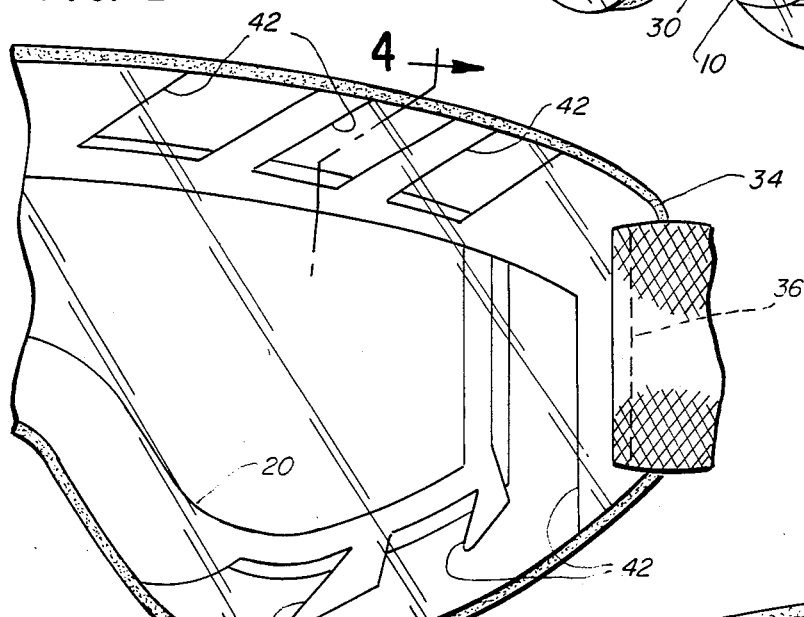
FIG. 2 is a fragmentary, enlarged elevation of the goggle from the front thereof.
Figure 3:
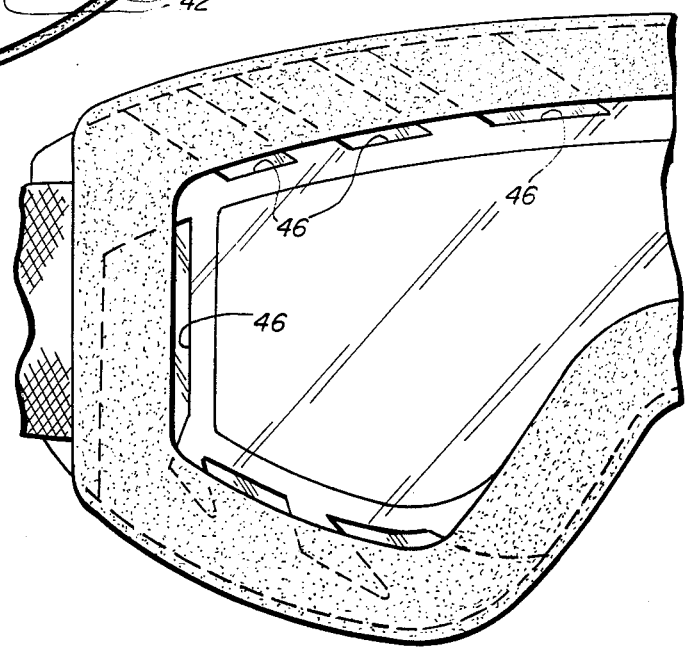
FIG. 3 is a fragmentary, enlarged elevation of the goggle from the rear thereof.
Figure 4:
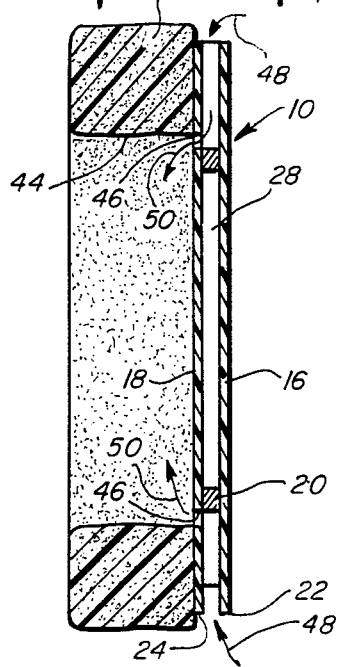
FIG. 4 is a sectional view taken approximately along the line 4—4 in FIG. 2.

The strap 12 is secured to the lens structure 10 at opposed ends 32 and 34 thereof. As best seen in FIG. 2, each of the lenses 16 and 18, at each of the ends 32 and 34, is provided with an aligned, vertically elongated slot 36 through which the strap 12 extends.

From the foregoing, it will be appreciated that the lens structure 10 has a convex side defined by the lens 16 and a concave side defined by the lens 18. Secured to the latter about the periphery of the lens 18 is the cushioning material 14. Preferably, the cushioning material is formed of a resilient, flexible, opened cell foam layer 40 of substantial thickness, generally at least ½" thick. The cushioning material 14 is adapted to cushioningly contact the face of the wearer of the goggle and conform thereto.

In a highly preferred embodiment of the invention, the goggle is also provided with anti-fogging means. Specifically, the spacer 20 is provided with a plurality of channels 42 at locations such as those indicated which open to the exterior of the goggle at various points about the edges 22 and 24 of the lenses 16 and 18. The channels 42 do not extend fully to the innermost boundary of the interconnecting means 20 but do extend inwardly of the innermost edge 44 of the layer 40. The inner lens 18 is in turn provided with a plurality of slot-like openings 46 disposed just inwardly of the layer 40 and in alignment with the innermost ends of the channels 42. As a consequence, in use, air may flow in the direction of arrows 48 past the edges 22 and 24 into the channels 42 and then through the openings 46 in the direction of arrows 50 to the concave side of the lens structure 10. This air flow causes the evaporation of any condensation on the concave surface of the lens structure 10 and/or prevents such condensation from occurring.

Preferably, the vent openings 46 in the lens 18 are formed therein by stamping simultaneously with the formation of the lens 18 itself.

From the foregoing, it will be appreciated that the invention provides a frameless goggle and a method of making the same. The goggle is highly advantageous in that by omitting the frame, manufacturing costs are considerably reduced. At the same time, because the goggle lens structure 10 is formed in the shape of a simple curve as opposed to a compound curve, there is sufficient flexibility so as to allow the goggle to conform generally to the face of any of a large variety of wearers having vastly differing facial proportions under the force applied by the strap 12 when on the head of a wearer. The thickness of the cushioning layer 40 serves to assure that contact with the face of the wearer is maintained about the entire periphery of the goggle and yet allows the same to be worn comfortably. In the preferred embodiment, the known advantages of a thermal lens are maintained and yet the goggle is provided with anti-fogging means as well through the unique provision of air channels in the spacer 20 and the inner lens 18. Thus, a simple, inexpensive, but highly adaptable and effective goggle structure results.

We claim:

1. A frameless goggle comprising:

inner and outer transparent, generally planar lenses in approximately parallel space relation and deformed into a simple curve;

a spacer being attached to and positioned between said lenses about the periphery of said lenses defining a viewing area through said lenses, said spacer having means for controlling air exchange into a space between said goggle and a wearer's face, said spacer maintaining said spaced relation and deformed simple curve;

a strap connected to at least one of said lenses at spaced locations;

a pliant, flexible cushioning edging secured to said inner lens and extending inwardly from the concave side of said simple curve to define the space between said goggle and the wearer's face; and said goggle being free of any external frame receiving or holding said lenses.

2. The frameless goggle of claim 1 wherein said spacer seals the interface of said lenses inwardly of the edges thereof to create a sealed viewing area; and said air exchange controlling means includes anti-fogging vents for allowing the flow of air to said concave side of said inner lens.

3. A frameless goggle comprising:
inner and outer transparent, generally planar lenses in approximately parallel space relation and deformed into a simple curve;
a spacer being attached to and positioned between said lenses about the periphery of said lenses defining a viewing area through said lenses, said spacer having means for controlling air exchange into a space between said goggle and a wearer's face, said spacer maintaining said spaced relation and deformed simple curve, said spacer seals the interface of said lenses inwardly of the edges thereof to create a sealed viewing area, said spacer is formed of a closed cell foam disposed between said lenses;
said air exchange controlling means includes anti-fogging vents for allowing the flow of air to said concave side of said inner lenses, said anti-fogging vents include channels in said foam extending to respective openings in said inner lens;
a strap connected to at least one of said lenses at spaced locations;
a pliant, flexible cushioning edging secured to said inner lens and extending inwardly from the concave side of said simple curve to define the space between said goggle and the wearer's face;
and said goggle being free of any external frame receiving or holding said lenses.

4. An anti-fogging lens construction comprising inner and outer transparent lenses in generally parallel spaced relation and each having aligned central parts defining a viewing area;
a non-rigid spacer sandwiched between said lenses peripherally about said viewing area and serving to seal the space between said lenses at said viewing area; and
air flow passages having spaced inlets and outlets and formed in at least said inner lens and said spacer with said outlets being located on the side of said inner lens remote from said spacer about said viewing area such that air flowing through said passages and exiting said outlets will tend to evaporate condensation on said inner lens side and/or prevent condensation from forming thereon.

5. The anti-fogging lens construction of claim 4 wherein at least one of said lenses has opposed ends each provided with a slot for receipt of a strap.

6. The anti-fogging lens construction of claim 4 wherein said inlets are defined by spaces between edges of said lenses.

7. The anti-fogging lens construction of claim 5 wherein said lenses have a curvature defined by a simple curve.

8. A goggle embodying the lens construction of claim 7 and further including a strap extending through said slots, and a foam cushion of substantial thickness secured directly to said lens construction and extending inwardly of said side of said inner lens peripherally about said viewing area, said outlets being disposed on the side of said cushion adjacent said viewing area.

9. The goggle of claim 8 wherein said form cushion is adhered to said side of said inner lens.

10. A method of manufacturing a frameless goggle construction which is adapted to fit a large variety of wearers, comprising:
(a) stamping an elongated, semi-rigid lens having opposed ends out of a generally planar sheet of transparent plastic material;
(b) providing a slot in each of the ends of the lens and vents in said lens simultaneously with step (a);
(c) curving the lens in the form of a simple curve such that it has a convex and a concave side;
(d) adhering a strip of foam to the concave side of the lens about the periphery thereof;
(e) disposing an elastic strap in said slots;
(f) applying a spacer with channels to said convex side such that said channels extend to said vents;
(g) applying a second lens to said spacer; and
(h) sealing said spacer to both said lenses.

11. A goggle construction comprising:
an elongated lens structure having inner and outer generally parallel transparent plastic lenses with concave and convex sides, said lenses having aligned central parts defining a viewing area and said inner lens having an outer part with an aperture defining an outlet through the inner lens;
a spacer being attached to and positioned between said lens with an inner portion extending peripherally about the entire viewing area to create a sealed viewing area, said spacer having an outer portion with a channel for the flow of air, said channel having a portion aligned with the outlet aperture on the inner lens;
a layer of soft, resilient cushioning material to cushion contact with and conform to the face of a wearer of the goggle, said cushioning material being mounted so as to extend inward from the concave side of the goggle; and
at least one air vent allowing passage of air from outside the goggle through said channel in the spacer to the outlet of the inner lens such that air flowing through said vent and exiting said outlet will tend to prevent condensation from forming on said concave side of the lens structure.

12. The goggle of claim 11 wherein said channel includes an air inlet between the edges of said lenses formed by an aperture in the edge of the spacer with the aperture being contiguous with the channel to cause air to enter at the side edge of the goggle and exit through the outlet in the inner lens.

13. The goggle of claim 11 wherein said inner lens has a plurality of apertures spaced from each other and defining a plurality of outlets spaced at least partly around the sealed viewing area, and the spacer includes channel portions aligned with the spaced apertures to cause air to exit at least partly around the concave side of the inner lens.

14. The goggle of claim 13 wherein said channel portions comprise a plurality of separate channels spaced from others of the channels formed in the spacer, with air entering the separate channels and flowing through and out corresponding spaced apertures of the inner lens.

* * * * *